United States Patent
Goto et al.

(10) Patent No.: US 10,773,726 B2
(45) Date of Patent: *Sep. 15, 2020

(54) INFORMATION PROVISION DEVICE, AND MOVING BODY

(71) Applicant: HONDA MOTOR CO., LTD., Tokyo (JP)

(72) Inventors: Shinichiro Goto, Saitama (JP); Hiromitsu Yuhara, Tokyo (JP); Tomoko Shintani, Tokyo (JP); Eisuke Soma, Tokyo (JP)

(73) Assignee: HONDA MOTOR CO., LTD., Tokyo (JP)

( * ) Notice: Subject to any disclaimer, the term of this patent is extended or adjusted under 35 U.S.C. 154(b) by 21 days.

This patent is subject to a terminal disclaimer.

(21) Appl. No.: 16/332,226

(22) PCT Filed: Jun. 22, 2017

(86) PCT No.: PCT/JP2017/023047
§ 371 (c)(1),
(2) Date: Mar. 11, 2019

(87) PCT Pub. No.: WO2018/061354
PCT Pub. Date: Apr. 5, 2018

(65) Prior Publication Data
US 2019/0300004 A1    Oct. 3, 2019

(30) Foreign Application Priority Data

Sep. 30, 2016 (JP) .................................. 2016-193787

(51) Int. Cl.
*B60W 50/00* (2006.01)
*B60W 40/09* (2012.01)
(Continued)

(52) U.S. Cl.
CPC ............ *B60W 40/09* (2013.01); *B60W 50/14* (2013.01); *G06K 9/00791* (2013.01);
(Continued)

(58) Field of Classification Search
CPC . B60W 2040/0854; B60W 2040/0863; B60W 50/10; B60W 2050/146;
(Continued)

(56) References Cited

U.S. PATENT DOCUMENTS 9,978,071 B2 * 5/2018 Kursar ............... G06Q 30/0261
2008/0105482 A1 * 5/2008 Yamaguchi ............ G05B 15/02
                                                    180/271
(Continued)

FOREIGN PATENT DOCUMENTS

JP    2005-128928 A    5/2005
JP    2007-269268 A    10/2007
(Continued)

OTHER PUBLICATIONS

International Search Report dated Sep. 12, 2017, issued in counterpart application No. PCT/JP2017/023047 (2 pages).

*Primary Examiner* — Hai Phan
*Assistant Examiner* — Son M Tang
(74) *Attorney, Agent, or Firm* — Westerman, Hattori, Daniels & Adrian, LLP

(57) ABSTRACT

An information provision device (60) includes: an emotion engine (66) which estimates an emotion of a test driver P1 of a vehicle (1); an action detection unit (65) which detects an action performed on the vehicle (1) by the test driver P1; a function-of-interest estimation unit (67) which estimates a specific function that interests the test driver P1 from among the functions possessed by the vehicle (1) based on the action of the test driver P1 detected by the action detection unit (65) and the emotion of the test driver P1 estimated by (Continued)

the emotion engine (66) when an action is detected; and an information provision unit (69) which provides the test driver P1 with information on the specific function.

14 Claims, 8 Drawing Sheets

(51) Int. Cl.
*B60W 50/14* (2020.01)
*G06K 9/00* (2006.01)
*G07C 5/08* (2006.01)
*G06Q 30/02* (2012.01)
*G08G 1/16* (2006.01)
*G09F 25/00* (2006.01)

(52) U.S. Cl.
CPC ......... *G06K 9/00845* (2013.01); *G06Q 30/02* (2013.01); *G07C 5/0841* (2013.01); *G08G 1/16* (2013.01); *G09F 25/00* (2013.01); *B60W 2050/146* (2013.01)

(58) Field of Classification Search
CPC .......... B60W 2540/22; G06K 9/00845; G06K 9/00993; G06Q 30/0265; G06Q 30/0266
See application file for complete search history.

(56) References Cited

U.S. PATENT DOCUMENTS

| | | | | |
|---|---|---|---|---|
| 2011/0083075 | A1* | 4/2011 | MacNeille | G10L 15/22 715/728 |
| 2012/0011477 | A1* | 1/2012 | Sivadas | G06F 3/015 715/866 |
| 2012/0150430 | A1* | 6/2012 | French | G01C 21/3453 701/425 |
| 2013/0035983 | A1* | 2/2013 | Kursar | G06Q 30/0205 705/7.29 |
| 2013/0054090 | A1* | 2/2013 | Shin | B60K 28/06 701/36 |
| 2014/0080098 | A1* | 3/2014 | Price | G09B 9/052 434/29 |
| 2014/0135598 | A1* | 5/2014 | Weidl | A61B 5/163 600/301 |
| 2014/0171752 | A1* | 6/2014 | Park | A61B 5/6893 600/301 |
| 2015/0352955 | A1* | 12/2015 | Mori | B60W 50/14 701/1 |
| 2016/0001781 | A1* | 1/2016 | Fung | G16H 50/20 701/36 |
| 2016/0104214 | A1* | 4/2016 | Larrinaga | G06Q 30/0278 705/306 |
| 2016/0351075 | A1* | 12/2016 | Hookham-Miller | G06F 3/0482 |
| 2017/0248441 | A1* | 8/2017 | Heimrath | B60W 50/0097 |
| 2018/0089605 | A1* | 3/2018 | Poornachandran | G06Q 10/06393 |
| 2018/0144549 | A1* | 5/2018 | Gonzalez | G02B 27/0172 |
| 2018/0174457 | A1* | 6/2018 | Taylor | G08G 1/0962 |
| 2018/0349254 | A1* | 12/2018 | Hui | G06F 11/3692 |
| 2019/0094959 | A1* | 3/2019 | Tan | B60K 37/02 |

FOREIGN PATENT DOCUMENTS

| | | |
|---|---|---|
| JP | 2008-261703 A | 10/2008 |
| JP | 2011-245060 A | 12/2011 |
| JP | 2016-16765 A | 2/2016 |

* cited by examiner

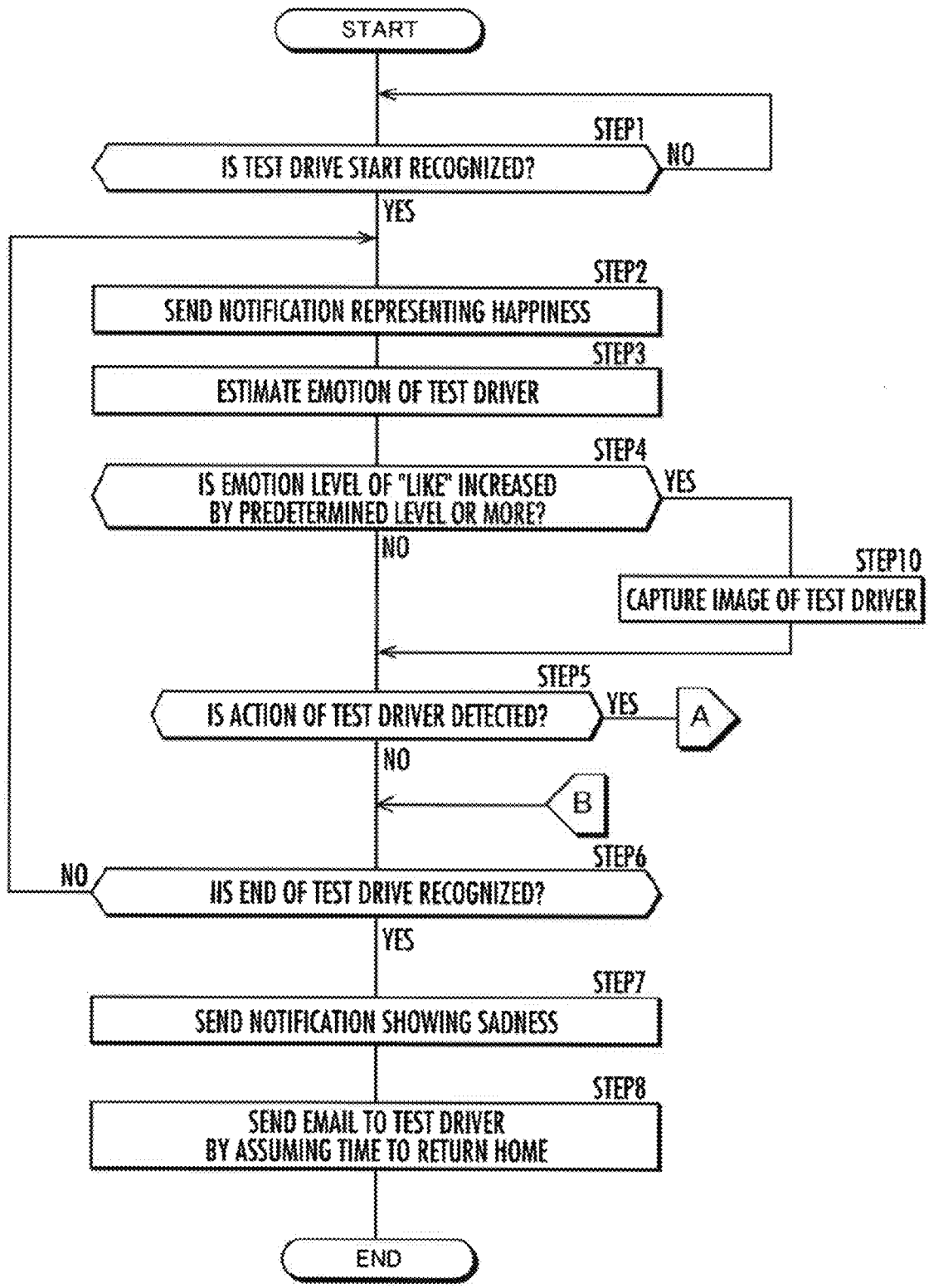

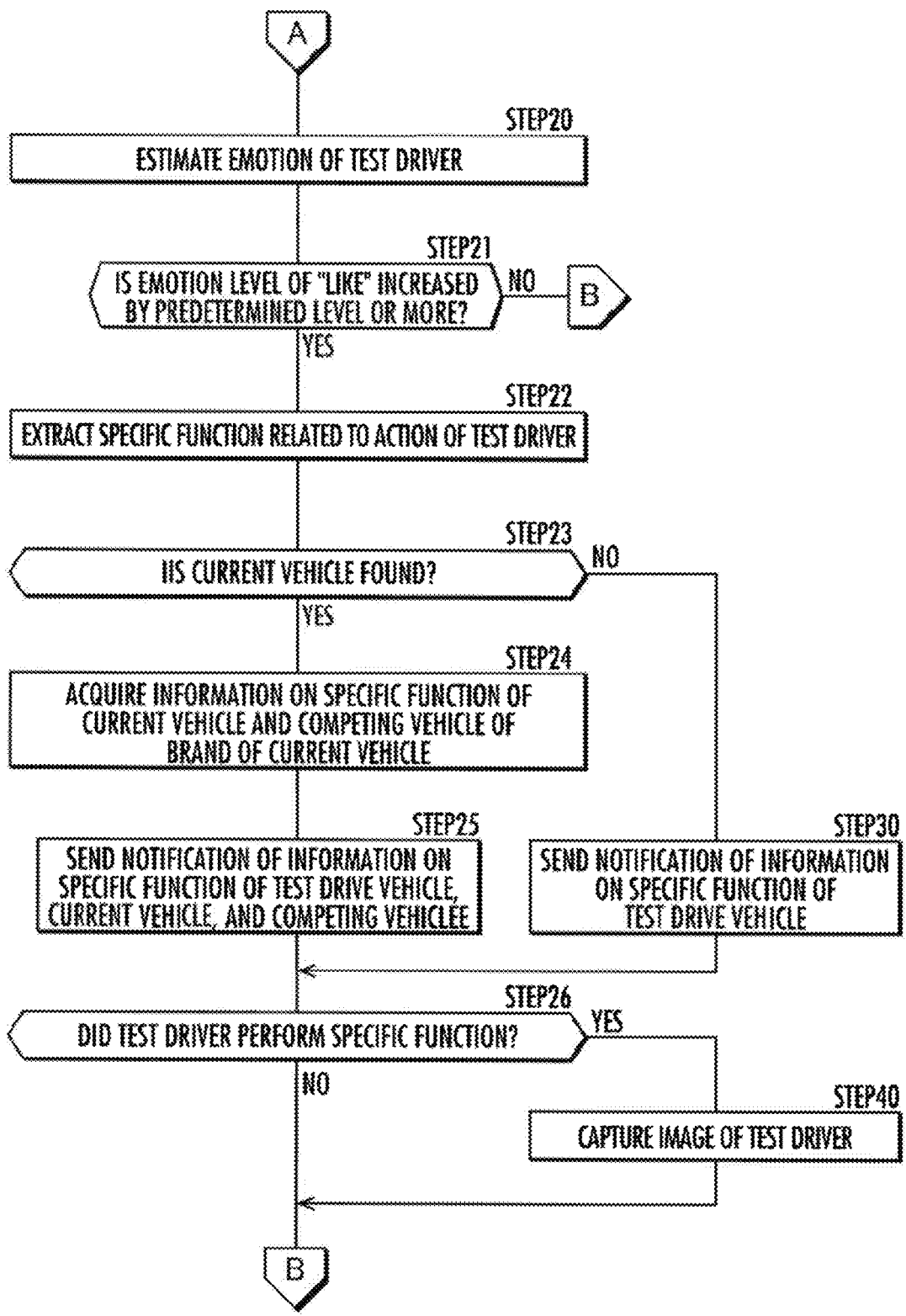

INFORMATION PROVISION DEVICE, AND MOVING BODY

TECHNICAL FIELD

The present invention relates to an information provision device which provides information on a moving body to a potential purchaser, a user, or the like, who is considering purchasing the moving body, and the moving body.

BACKGROUND ART

There has conventionally been proposed an information provision device for use in promoting sales of a vehicle when a potential purchaser is visiting a car dealer, and a customer service support method using the information provision device (for example, see Patent Literature 1).

The information provision device disclosed in Patent Literature 1 transmits, to a mobile terminal of the salesperson, data on customer service conditions (response speed, explanation level, and requirements), which are desired by the potential purchaser, entered into a terminal installed at an entrance of the dealer, data indicating the customer information and recommended products based on the past purchase history and preference of the potential purchaser, and other data.

Thus, the salesperson can proceed with negotiations with the potential purchaser by referring to customer service conditions, customer information, recommended products, and the like displayed on a display unit of a mobile terminal.

CITATION LIST

Patent Literature

Patent Literature 1: Japanese Patent Laid-Open No. 2005-128928

SUMMARY OF INVENTION

Technical Problem

The potential purchaser who is considering purchasing a moving body such as a vehicle often visits a retail store to receive an explanation of the moving body from a salesperson and then test-drives the moving body. For test drive, the potential purchaser enters a moving body prepared for test driving and checks the functions provided in the moving body. Since the functions provided in the moving body are diversified, it is difficult for the salesperson to identify and introduce the functions that interest the potential purchaser during the limited test drive time.

Further, the users of the moving body (such as owners of the moving body) other than the potential purchasers rarely recognize and use all of the diversified functions provided in the moving body. Thus, it is expected to increase the satisfaction level of the users to the moving body by introducing the functions that interest the users and encouraging the use of those functions.

An object of the present invention, which has been made in view of such a background, is to provide an information provision device and a moving body which can identify a function that interests the user from among the functions provided in the moving body and can provide the user of the moving body with information thereon.

Solution to Problem

A first aspect of an information provision device of the present invention is
an information provision device which functions in a moving body, the information provision device comprising:
an emotion estimation unit which estimates an emotion of a user of the moving body;
a function-of-interest estimation unit which estimates a specific function that interests the user from among the functions possessed by the moving body based on the emotion of the user estimated by the emotion estimation unit; and
an information provision unit which provides the user with information on the specific function.

According to the present invention, the emotion estimation unit estimates an emotion of the user and the function-of-interest estimation unit estimates a specific function that interests the user from among the functions possessed by the moving body based on the emotion of the user estimated by the emotion estimation unit. Then, the situation provision unit provides the user with information on the specific function. Thus, the specific function that the user is interested in while using the moving body can efficiently appeal to the user and can give the user a good impression of the moving body.

Further, the first aspect comprises an action detection unit which detects an action performed on the moving body by the user, wherein
the function-of-interest estimation unit estimates the specific function based on the action of the user detected by the action detection unit and the emotion of the user estimated by the emotion estimation unit when the action is detected.

According to this configuration, the specific function is estimated based on the action of the user detected by the action detection unit and the emotion of the user estimated by the emotion estimation unit when the action is detected. Thus, by reflecting the emotion of the user when the action of the user is detected, the specific function estimated by the function-of-interest estimation unit can be better meet the interest of the user.

Then, a second aspect of the information provision device of the present invention is
an information provision device which functions in a moving body, the information provision device comprising:
an action detection unit which detects an action performed on the moving body by the user of the moving body;
a function-of-interest estimation unit which estimates a specific function that interests the user from among the functions possessed by the moving body based on the action of the user detected by the action detection unit; and
an information provision unit which provides the user with the information on the specific function.

According to the present invention, the action of the user is detected by the action detection unit, and the specific function that interests the user is estimated from among the functions possessed by the moving body by the function-of-interest estimation unit based on the action of the user detected by the action detection unit. Then, the situation provision unit provides the user with the information on the specific function. Thus, the specific function related to the action of the user can efficiently appeal to the user and can give the user a good impression of the moving body.

Further, the information provision device comprises an operation situation detection unit which detects an operation performed by the user on an operation unit provided in the moving body, wherein
the action detection unit detects an action performed on the moving body by the user based on a detection result of the operation situation detection unit.

According to this configuration, the action detection unit can easily detect the action of the user by causing the operation situation detection unit to detect the operation situation of each of various operation units provided in the moving body.

Further, the information provision unit provides information encouraging operation for using the specific function as the information on the specific function.

According to this configuration, the user can be encouraged to actually experience a specific function assumed to interest the user by providing information encouraging operation for using the specific function as the information on the specific function.

Further, the information provision device comprises a surrounding situation recognition unit which recognizes a situation around the moving body, wherein when the specific function is a function for improving driving performance, on condition that the surrounding situation recognition unit recognizes that the road on which the moving body is moving is empty, the information provision unit provides the information encouraging operation for using the specific function.

According to this configuration, under limited circumstances where it is determined that there is no problem for driving from the surrounding road conditions, the user can be encouraged to experience the function for improving driving performance.

Further, the information provision device comprises:

a test drive recognition unit which recognizes that the user is test-driving the moving body and a current moving body information acquisition unit which acquires information on a current moving body owned by the user, wherein while the test drive recognition unit recognizes that the user is test-driving the moving body, the information provision unit provides the user with information on the specific function of the current moving body recognized from the information on the current moving body together with the information on the specific function of the moving body that the user is test-driving.

According to this configuration, the user can be made to recognize an advantage of replacing the current moving body with the moving body that the user is test-driving by providing the user (test driver) with information on both moving bodies, the information including the specific functions assumed to interest the user.

Further, while the test drive recognition unit recognizes that the user is test-driving the moving body, the information provision unit provides the user with information on the specific function of a competing moving body competing with the moving body that the user is test-driving from a brand of the current moving body recognized from the information of the current moving body, together with the information on the specific function of the current moving body and the moving body that the user is test-driving.

According to this configuration, when the current moving body of the user (test driver) is different from the brand (such as the manufacturer) of the moving body that the user is test-driving, the user is provided with information on both the competing moving body and the moving body that the user is test-driving in terms of the specific function assumed to interest the user. By doing so, the user can be made to recognize functional differences due to differences in brands and can be encouraged to change the brand of the moving body that the user is using.

Further, the information provision device comprises a test drive recognition unit which recognizes that the user is test-driving the moving body and a current moving body information acquisition unit which acquires information on a current moving body owned by the user, wherein while the test drive recognition unit recognizes that the user is test-driving the moving body, the information provision unit provides the user with information on the specific function of a competing moving body competing with the moving body that the user is test-driving from a brand of the current moving body recognized from the information of the current moving body, together with the information on the specific function of the moving body that the user is test-driving.

According to this configuration, the user can be made to recognize an advantage of replacing the current moving body with the moving body that the user is test-driving by providing the user (test driver) with information on both moving bodies including the specific functions assumed to interest the user.

Further, the information provision device comprises:

a test drive recognition unit which recognizes that the user is test-driving the moving body;

a notification unit which notifies the user; and a moving body emotion notification unit wherein while the test drive recognition unit recognizes that the user is test-driving the moving body, the notification unit notifies that the moving body is happy, and when it is switched from a state in which the test drive recognition unit recognizes that the user is test-driving the moving body, to a state in which the test drive recognition unit does not recognize that the user is test-driving the moving body, the notification unit notifies that the moving body feels sad.

According to this configuration, the notification that the moving body is happy can give the user (test driver) an impression that the moving body is enjoying driving with the user during test driving, and thus can enhance the user's affinity to the moving body. Further, at the end of test driving, the notification that the moving body feels sad can make the user feel sad to leave, which can encourage the user to continue to consider purchasing.

Then, a moving body of the present invention comprises any one of the above described information provision devices. The moving body comprising the information provision device can exert the same operational effects as the above described information provision devices and thereby can effectively increase the reputation level of the user to the moving body.

BRIEF DESCRIPTION OF DRAWINGS

FIG. 4 is a first flowchart of the information provision device.

FIG. 5 is a second flowchart of the information provision device.

FIG. 6A illustrates a situation where the vehicle is being stopped, and FIG. 6B illustrates a situation where the vehicle is traveling.

FIG. 7A illustrates an example of an emotion notification while the vehicle is traveling, and FIG. 7B illustrates an example of an emotion notification while the test drive is finished.

DESCRIPTION OF EMBODIMENTS

Hereinafter, embodiments of the present invention will be described with reference to FIGS. 1 to 8.

Figure 1:
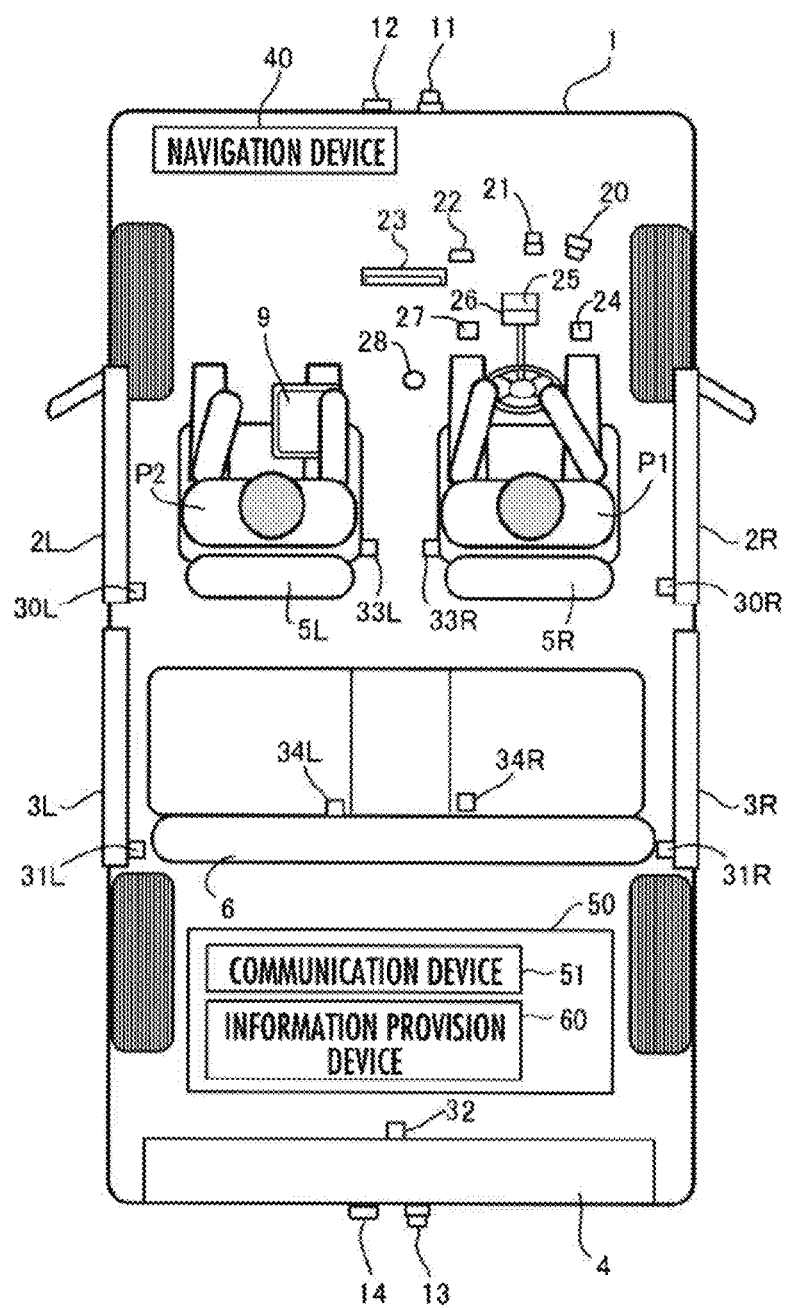
FIG. 1 is an explanatory view of a four-wheeled vehicle (moving body) having an information provision device mounted thereon.

1. Configuration of a Vehicle Having an Information Provision Device Mounted Thereon As illustrated in FIG. 1, an information provision device 60 is mounted on a four-wheeled vehicle 1 (which corresponds to a moving body of the present invention and hereinafter referred to as a vehicle 1). Note that the information provision device 60 of the present embodiment is a vehicle-mounted type, but the information provision device of the present invention may be a portable type which can be carried by a user and can be brought into a vehicle for use.

FIG. 1 illustrates a situation where a test driver P1 (which corresponds to the user of the present invention), who is a potential purchaser and is considering purchasing the same type of the vehicle 1, sits on a driver's seat 5R of the vehicle 1, and a salesperson P2 in charge of sales of the vehicle sits on a passenger seat 5L. The salesperson P2 carries a business terminal 9 (such as a tablet and a smartphone) and provides a customer service to the test driver P1 through the business terminal 9.

The vehicle 1 comprises a front camera 11, a front radar 12, a rear camera 13, and a rear radar 14 as the configuration for recognizing the surrounding situation of the vehicle 1, and comprises a navigation device 40 having a global positioning system (GPS) unit 41 and a map database (DB) 42 to be detailed later as the configuration for acquiring route information to the destination.

As the configuration for recognizing the situation of the driver of the vehicle 1, the vehicle 1 comprises a driver's seat camera 20 which captures an image of at least a face portion of the driver and a driver's seat microphone 21 which enters driver's voice.

As the configuration for detecting an operation performed by a driver on a vehicle operation unit, the vehicle 1 comprises: a steering angle sensor 25 which detects a steering angle of a steering wheel; a torque sensor 26 which detects a steering torque applied to the steering wheel; an accelerator pedal sensor 24 which detects a depression amount of an accelerator pedal; a brake pedal sensor 27 which detects a depression amount of a brake pedal; and a sports mode switch 28 which accepts setting and releasing of a sports mode (a driving mode with improved response, such as control of great increase in driving force relative to accelerator operation).

The vehicle 1 comprises door sensors 30R, 30L, 31R, 31L, and 32 which detect opening and closing of front doors 2R, and 2L, rear doors 3R, and 3L, and back door 4; and seat sensors 33R, 33L, 34R, and 34L which detect the presence or absence of a seated occupant on each of a driver's seat 5R, a passenger seat 5L, and a rear seat 6. Further, the vehicle 1 comprises a speaker 22 (which corresponds a notification unit of the present invention) and a display unit 23 (which corresponds the notification unit of the present invention) for notifying a passenger.

The vehicle 1 comprises a control unit 50 which controls the overall operation of the vehicle 1. The control unit 50 is an electronic circuit unit including a CPU, a memory, various interface circuits, and the like, which are not illustrated. The control unit 50 comprises a communication device 51 and an information provision device 60.

The control unit 50 receives data imaged by the front camera 11, the rear camera 13, and the driver's seat camera 20, and data of an object position detected by the front radar 12 and the rear radar 14. The control unit 50 receives signals detected by the steering angle sensor 25, the torque sensor 26, the accelerator pedal sensor 24, the brake pedal sensor 27, the door sensors 30R, 30L, 31R, 31L, and 32, and the seat sensors 33R, 33L, 34R, and 34L.

Further, the control unit 50 receives an audio signal inputted into the driver's seat microphone 21. In addition, the control unit 50 communicates with the navigation device 40 and communicates with the business terminal 9 and the like via the communication device 51.

In addition, the control unit 50 outputs control signals to control the operation of the speaker 22, the display unit 23, the communication device 51, the navigation device 40, and the like.

2. Configuration of the Information Provision Device

Figure 2:
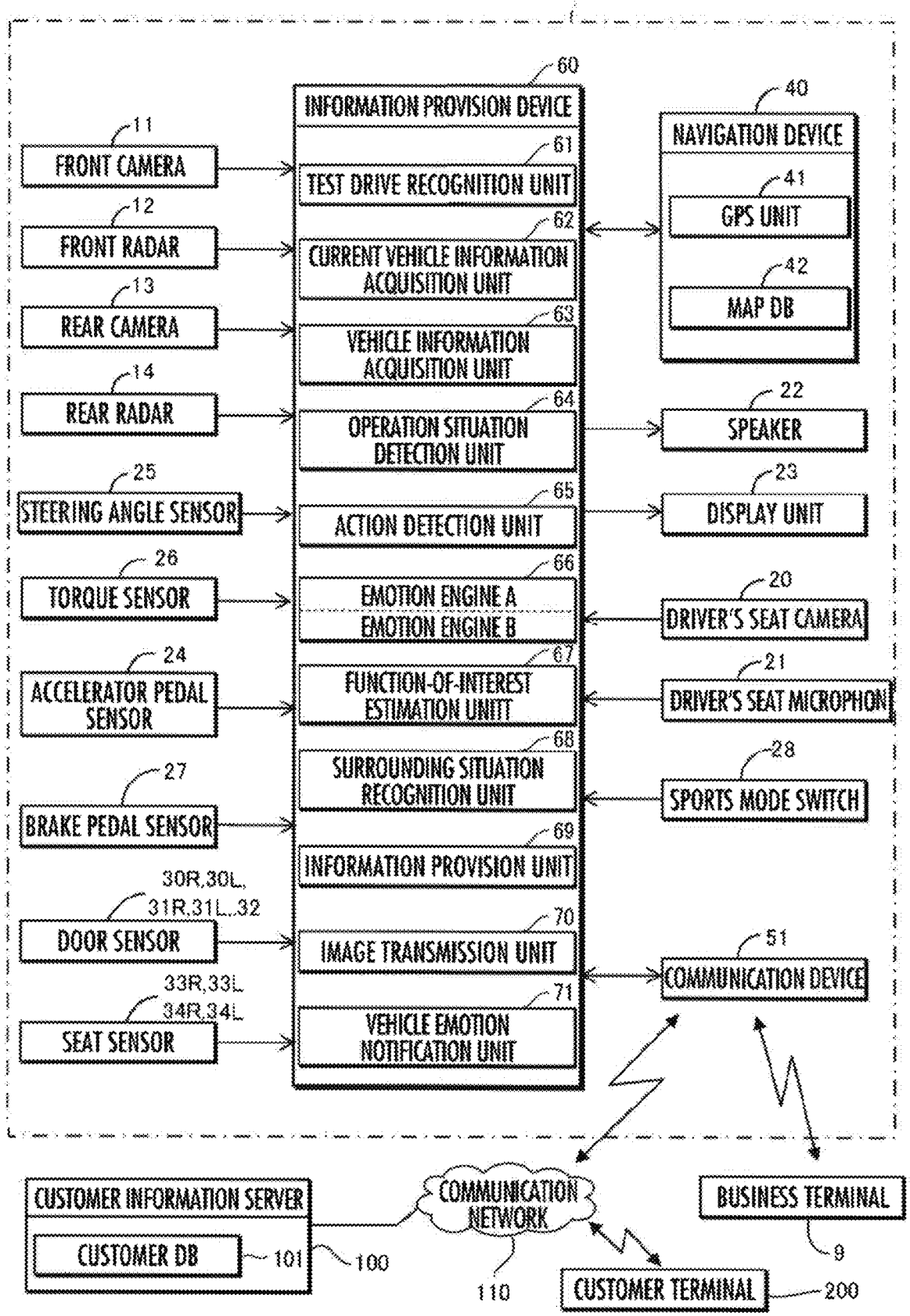
FIG. 2 is a control block diagram of the information provision device.

Then, with reference to FIG. 2, the information provision device 60 is formed of the CPU which executes the control programs for the information provision device 60 stored in the memory of the control unit 50. The information provision device 60 comprises a test drive recognition unit 61, a current vehicle information acquisition unit 62 (which corresponds to the current moving body information acquisition unit of the present invention), a vehicle information acquisition unit 63, an operation situation detection unit 64, an action detection unit 65, an emotion engine 66 (which corresponds to the emotion estimation unit of the present invention), a function-of-interest estimation unit 67, a surrounding situation recognition unit 68, an information provision unit 69, an image transmission unit 70, and a vehicle emotion notification unit 71 (which corresponds to the moving body emotion notification unit of the present invention).

The test drive recognition unit 61 recognizes that the test drive of the vehicle 1 is performed, by the communication with the business terminal 9 or the like. The current vehicle information acquisition unit 62 acquires information on a vehicle (current vehicle) currently owned by the test driver P1, who is test-driving the vehicle 1, by accessing a customer database (DB) 101 of a customer information server 100 via a communication network 110.

The vehicle information acquisition unit 63 acquires information on the ON/OFF of an ignition switch (unillustrated) of the vehicle 1, the operation of a safety device system (unillustrated) (operation of an advanced driver assistance systems (ADAS), an antilock brake system (ABS), an air bag, an emergency call, and the like), vehicle speed, acceleration/deceleration, and the like, through a control area network (CAN) or the like. The operation situation detection unit 64 detects the operation situation of each operation unit of the vehicle 1 operated by the test driver P1 based on the signal detected by each of the sensors 24 to 27, 30R, 30L, 31R, 31L, 32, 33R, 33L, 34R, and 34L.

The action detection unit 65 detects the action of the test driver P1 based on the operation situation of each operation unit detected by the operation situation detection unit 64, the situation of the test driver P1, who is driving or located around the vehicle 1, and which is recognized from the images captured by the cameras 11, 13, and 20, and the voice or the like of the test driver P1 inputted into the driver's seat microphone 21.

The emotion engine 66 includes an emotion engine A which estimates the emotion of a driver of the vehicle 1 (herein the test driver P1) and an emotion engine B which generates an emotion of the vehicle 1 by personifying the vehicle 1.

Figure 3:
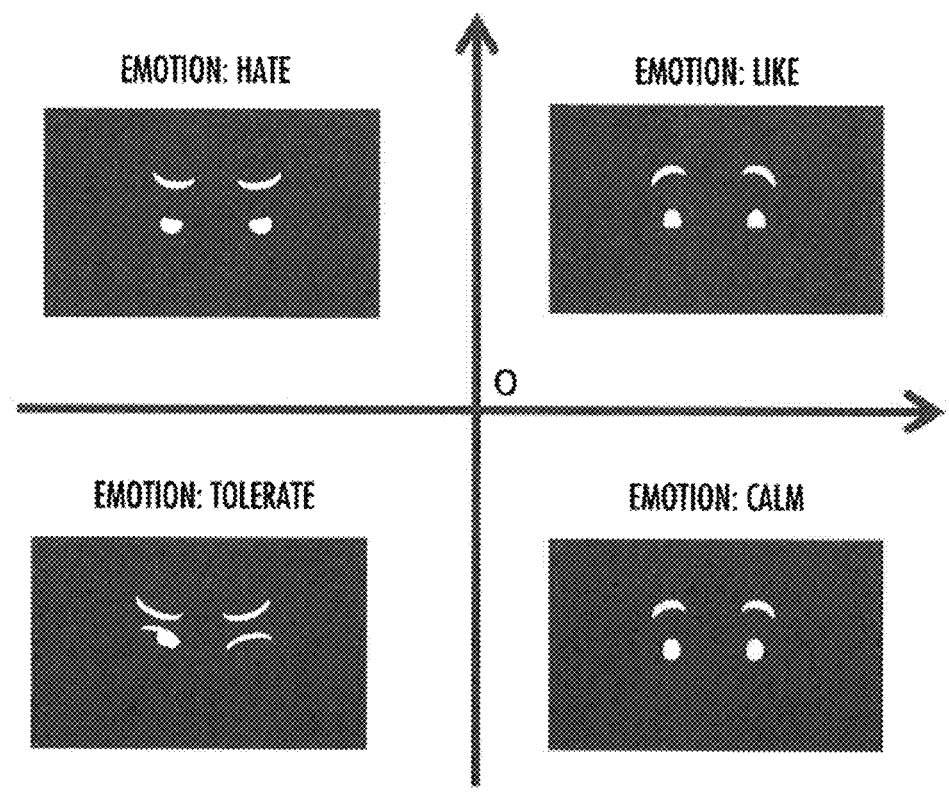
FIG. 3 is an explanatory view of an emotion engine.

As illustrated in FIG. 3, the emotion engine A quantifies the facial expression of the test driver P1 recognized from the image captured by the driver's seat camera 20; the tone and intonation of voice of the test driver P1 inputted into the driver's seat microphone 21; the operation situation of each operation unit operated by the test driver P1 and detected by the operation situation detection unit 64; and the vehicle information acquired by the vehicle information acquisition unit 63, all of which are plotted on the horizontal axis (axis of calmness) and the vertical axis (axis of steady state) as illustrated in FIG. 3.

Then, based on the quadrants (first quadrant: like, second quadrant: hate, third quadrant: tolerate, and fourth quadrant: calm) to which the plotted points belong and the position of each point in the corresponding quadrant, the degree of each emotion (emotion level) of the test driver P1 (like: the first quadrant, hate: the second quadrant, tolerate: the third quadrant, and calm: the fourth quadrant) is estimated and outputted.

Note that in the present embodiment, the emotion engine 66 uses the facial expression of the test driver P1, the voice of the test driver P1, the operation situation of each operation unit of the vehicle 1, and the vehicle information of the vehicle 1 to estimate the emotion level of the test driver P1, but at least the facial expression and the voice of the test driver P1 may be used to estimate the emotion of the test driver P1. Note also that other factors such as the profile (preference, age, sex, and the like) of the test driver P1 recognized from the customer data of the test driver P1, the biometric information (pulse rate, heart rate, blood pressure, and the like detected by biological sensors) of the test driver P1, the grip condition of the steering wheel gripped by the test driver P1 may be used to estimate the emotion level of the test driver P1.

Further, the emotion engine B quantifies the operation situation of each operation unit of the vehicle 1 detected by the operation situation detection unit 64, the vehicle information of the vehicle 1 acquired by the vehicle information acquisition unit 63, and other information, all of which are plotted on the horizontal axis (axis of calmness) and the vertical axis (axis of steady state) in the same manner as the emotion engine A as illustrated in FIG. 3. Then, based on the quadrants to which the plotted points belong and the position of each point in the corresponding quadrant, the degree (emotion level) of each emotion (like, hate, tolerate, and calm) of the personified vehicle 1 is generated and outputted.

Based on the emotion level of the test driver P1 estimated by the emotion engine A, the function-of-interest estimation unit 67 estimates a specific function assumed to interest the test driver P1 among the functions provided in the vehicle 1.

Based on the images around the vehicle 1 detected by the front camera 11 and the rear camera 13; the objects around the vehicle 1 detected by the front radar 12 and the rear radar 14; traffic information around the vehicle 1 received from the navigation device 40; and other information, the surrounding situation recognition unit 68 recognizes the situation of the road on which the vehicle 1 is travelling.

During the test drive, the vehicle emotion notification unit 71 sends a notification representing the emotion of the vehicle 1 by personifying the vehicle 1 to be detailed later.

3. Information Provision Processing

Then, with reference to the flowchart illustrated in FIG. 4, information provision processing executed by the information provision device 60 for the test driver P1 will be described.

Figure 6A:
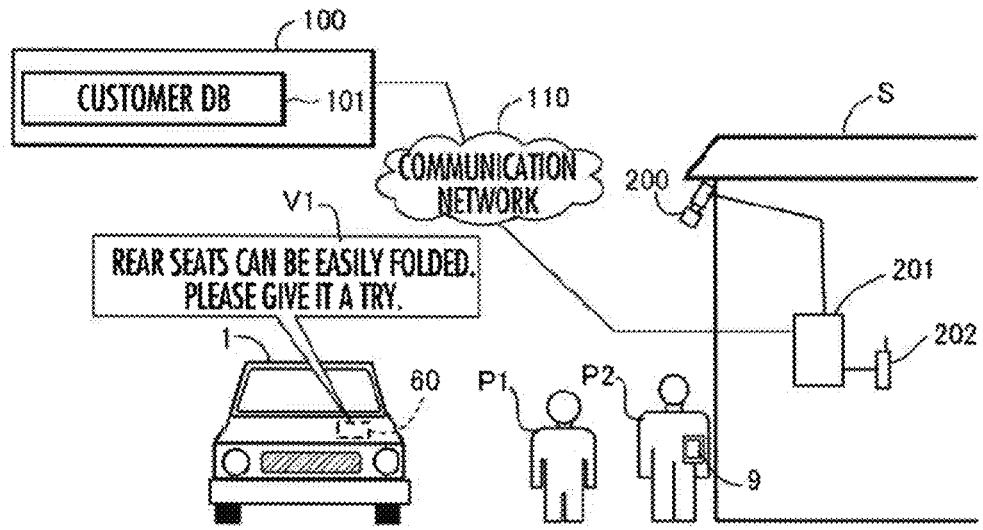
FIGS. 6A and 6B are first explanatory views illustrating an operating situation of the information provision device during test drive.

STEP 1 is a process performed by the test drive recognition unit 61. The test drive recognition unit 61 recognizes that the test driver P1 is test-driving the vehicle 1. As illustrated in FIG. 6A, when the test driver P1, who is a potential purchaser of a vehicle, visits a store S of a car dealer, the test driver P1 is captured by a store camera 200 installed at an entrance of the store S, and the captured image data is transmitted to a personal computer 201 located in the store S.

The personal computer 201 analyzes the face image of the test driver P1 and accesses a customer DB 101 held by the customer information server 100 to determine whether the test driver P1 is a new customer (no customer data) or an existing customer (customer data being present). If the test driver P1 is an existing customer, the customer data of the test driver P1 acquired from the customer DB 101 (including the profile, preference, past transaction history, and the like of the test driver P1) is transmitted to the business terminal 9 of the salesperson P2 in charge of the test driver P1 to notify that the test driver P1 has come to the store.

Here, the communication between the business terminal 9 and the personal computer 201 may be performed via the communication network 110 or may be performed by wireless LAN via a wireless router 202 connected to the personal computer 201.

Meanwhile, if the test driver P1 is a new customer, the personal computer 201 selects an appropriate salesperson P2, and transmits, to the business terminal 9 of the selected salesperson P2, data notifying that the test driver P1 has come to the store. In this case, when starting a customer service of the test driver P1 who is a new customer, the salesperson P2 confirms the profile and the like of the test driver P1 to newly generate customer data for the test driver P1.

For the customer service of the test driver P1, the salesperson P2 notifies that the vehicle 1 for test drive is ready and persuades the customer to have a test drive. When the test driver P1 wants to have a test drive, the salesperson P2 transmits, to the information provision device 60 of the vehicle 1, test drive start notification data notifying that the test driver P1 will start test driving and customer data of the test driver P1.

When the test drive start notification data is received, the test drive recognition unit 61 recognizes that the test driver P1 starts the test drive. Then, the process moves to STEP 2. Alternatively, the test drive recognition unit 61 may analyze a conversation voice between the test driver P1 and the salesperson P2 inputted into the driver's seat microphone 21 and from the analysis result, may recognize that test driver P1 performs the test drive.

When an ON (detection state) signal is outputted from the seat sensor 33R of the driver's seat 5R, the test drive recognition unit 61 recognizes that the test driver P1 has got on the vehicle 1, and when the seat sensor 33R indicates an ON state, the test drive recognition unit 61 recognizes that the test driver P1 is test-driving.

Further, from the vehicle information acquired by the vehicle information acquisition unit 63 and the current position of the vehicle 1 acquired by the navigation device 40, the test drive recognition unit 61 recognizes that the vehicle 1 starts test-driving, is test-driving, or ends test-driving.

Based on the change in the current position of the vehicle 1 acquired by the navigation device 40, when it is detected that the vehicle 1 has returned to the store S, and when the output from the seat sensor 33R is switched from the ON signal (detection state) to the OFF state (non-detection state) and the output from the door sensor 30R of the front door 2R on the driver's seat side is switched from the ON signal (detection state) to the OFF state (non-detection state), the test drive recognition unit 61 recognizes that the test drive has ended.

Alternatively, the test drive recognition unit 61 may analyze the conversation voice between the test driver P1 and the salesperson P2 inputted into the driver's seat microphone 21, and from the analysis result (a voice analysis of the salesperson P2 saying, for example, "Thank you very much for your test drive"), the test drive recognition unit 61 may recognize that the test drive of the test driver P1 has ended.

Figure 7A:
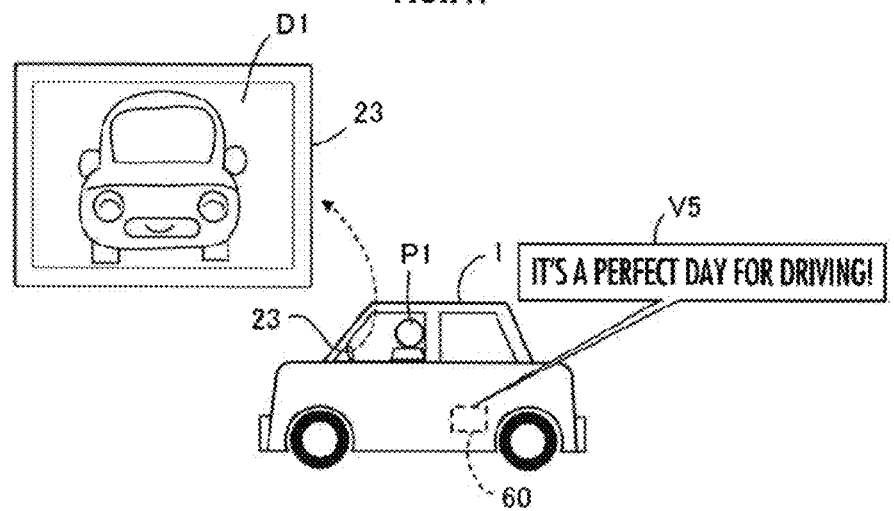
FIGS. 7A and 7B are explanatory views where the information provision device notifies the test driver of vehicle emotions during test drive.

The following STEP 2 is a process performed by the vehicle emotion notification unit 71. While the test drive recognition unit 61 recognizes that the test drive is being performed, the vehicle emotion notification unit 71 sends a notification representing that the vehicle 1 is happy, in STEP 2 as illustrated in FIG. 7A. More specifically, the vehicle emotion notification unit 71 displays, on the display unit 23, an image D1 personifying the state in which the vehicle 1 is happy and at the same time outputs a voice V5 saying, for example, "It's a perfect day for driving!" with a bright tone from the speaker 22.

Alternatively, according to the emotion level "like" of the vehicle 1 outputted from the emotion engine B, the higher the emotion level, the higher the degree of happiness expressed by the image D1 and the voice V5 may be.

The following STEP 3 is a process performed by the emotion engine A. The emotion engine A performs the above described emotion estimation process at a predetermined sampling period and outputs the level of each emotion (like, hate, tolerate, and calm) of the test driver P1 as needed. The following STEP 10 branched from STEP 4 and STEP 5 is a process performed by the image transmission unit 70. In STEP 4, the image transmission unit 70 determines whether or not the emotion level of "like" outputted from the emotion engine A is increased by a predetermined level or more.

Then, if the emotion level of "like" is increased by a predetermined level or more, the process is branched to STEP 10, where the image transmission unit 70 captures an image of the test driver P1 by the driver's seat camera 20 and holds data of the captured image in memory. Then, the process moves to STEP 5. Note that the image may be a still image or a moving image. Meanwhile, if the emotion level of "like" is not increased by a predetermined level or more, the process moves to STEP 5.

STEP 5 and STEP 20 to STEP 22 in FIG. 5 branched from STEP 5 are processes performed by the function-of-interest estimation unit 67. In STEP 5, the function-of-interest estimation unit 67 determines whether or not the action detection unit 65 detects an action of the test driver P1. Then, if an action of the test driver P1 is detected, the process is branched to STEP 20 in FIG. 5. If no action of the test driver P1 is detected, the process moves to STEP 6.

In STEP 20, the function-of-interest estimation unit 67 detects the emotion level of the test driver P1 from the output of the emotion engine A. In the following STEP 21, the function-of-interest estimation unit 67 determines whether or not the emotion level of "like" of the test driver P1 is increased by a predetermined level or more. Then, if the emotion level of "like" of the test driver P1 is increased by a predetermined level or more, the process moves to STEP 22. If the emotion level of "like" of the test driver P1 is not increased by a predetermined level or more, the process moves to STEP 6 in FIG. 4.

In STEP 22, the function-of-interest estimation unit 67 extracts a specific function of the vehicle 1 related to the action of the test driver P1 detected in STEP 5. For example, when an action that the test driver P1 opens or closes the back door 4 of the vehicle 1 is detected (when the test driver P1 opens or closes the back door 4, the emotion of "like" of the test driver P1 increases), the function-of-interest estimation unit 67 extracts "rear seat folding function" for enlarging the luggage compartment as the function related to this action.

For example, when an action that the test driver P1 steps on the accelerator pedal to accelerate the vehicle 1 is detected (when the test driver P1 performs an acceleration operation, the emotion of "like" of the test driver P1 is increased), the function-of-interest estimation unit 67 selects "sports mode function" as the function related to this action.

The following STEP 23 to STEP 25, and STEP 30 are processes performed by the information provision unit 69. In STEP 23, the information provision unit 69 determines the presence or absence of the current vehicle (which corresponds to the current moving body of the present invention) of the test driver P1 from the customer data of the test driver P1. Then, if a current vehicle is found, the process moves to STEP 24, where the information provision unit 69 acquires information on a specific function of the current vehicle and a vehicle (competing vehicle) competing with the vehicle 1 of the brand of the current vehicle (generally the manufacturer of the current vehicle).

For example, when the specific function is "sports mode function", the information provision unit 69 acquires information on "sports mode function" (presence or absence of the sports mode function, elements to be changed by the sports mode function, and the like) of the current vehicle of the test driver P1 and "sports mode function" of a competing vehicle (which corresponds to the competing moving body of the present invention).

Then, in the following STEP 25, the information provision unit 69 notifies the test driver P1 of the information on the specific function of the vehicle 1, the current vehicle, and the competing vehicle by display on the display unit 23 and voice output from the speaker 22. From this notification, the test driver P1 can recognize the specific function of the vehicle 1 in terms of the difference between the current vehicle and the competing vehicle and the advantage thereof.

Meanwhile, if no current vehicle of the test driver P1 is found, the process is branched from STEP 23 to STEP 30, where the information provision unit 69 sends only the information on the specific function of the vehicle 1.

As used herein, the information on the specific function of the vehicle 1 includes information encouraging the use of the specific function. For example, FIG. 6A illustrates a notification sent when "rear seat folding function" is estimated as the specific function that interests the test driver P1, and the information provision unit 69 uses the speaker 22 to output a voice message V1 saying "The rear seats can be easily folded. Please give it a try". Further, the information provision unit 69 outputs, to the display unit 23, a video explaining the rear seat folding procedure.

Figure 6B:
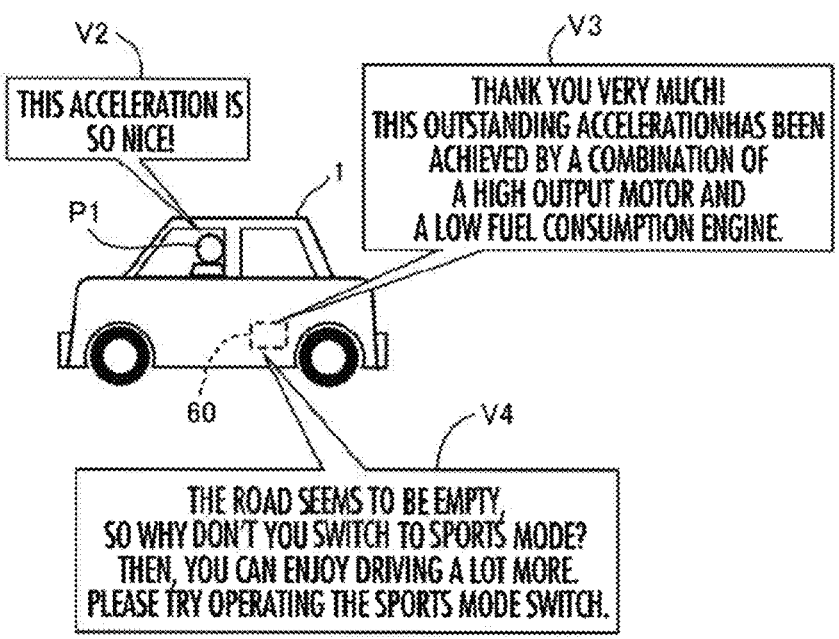

Further FIG. 6B illustrates a notification sent when "sports mode function" is estimated as the specific function that interests the test driver P1. More specifically, when the test driver P1 performs an acceleration operation and says that "This acceleration is so nice!", which voice V2 is inputted into the driver's seat microphone 21. In response to the voice V2, the information provision unit 69 uses the speaker 22 to output a voice V3 saying "Thank you very much! This outstanding acceleration has been achieved by a combination of a high output motor and a low fuel consumption engine." to appeal the driving performance of the vehicle 1.

Then, on condition that the surrounding situation recognition unit 68 recognizes that the road on which the vehicle 1 is traveling is empty, the information provision unit 69 uses the speaker 22 to output a voice V4 saying that "The road seems to be empty, so why don't you switch to sports mode? Then, you can enjoy driving a lot more. Please try operating the sports mode switch". Further, the information provision unit 69 outputs, to the display unit 23, a video displaying the position (such as near a shift lever) in which the sports mode switch 28 is placed.

The following STEP 26 and STEP 40 branched from STEP 26 are processes performed by the image transmission unit 70. In STEP 26, the image transmission unit 70 uses the operation situation detection unit 64 to determine whether or not the test driver P1 performed the operation of the specific function.

Then, if the test driver P1 performed the operation of the specific function, the process is branched to STEP 40, and if the test driver P1 did not perform the operation of the specific function, the process moves to STEP 6 in FIG. 4. In STEP 40, the image transmission unit 70 uses the driver's seat camera 20 to image the test driver P1 and hold the imaged data in memory, and then the process moves to STEP 6 in FIG. 4.

STEP 6 and STEP 7 in FIG. 4 are processes performed by the vehicle emotion notification unit 71. In STEP 6, the vehicle emotion notification unit 71 determines whether or not the test drive recognition unit 61 recognizes that the test driver P1 ends the test drive of the vehicle 1. Then, if the end of the test drive is recognized, the process moves to STEP 7, and if the end of the test drive is not recognized, the process returns to STEP 2, where the process following STEP 2 is executed again.

Figure 7B:
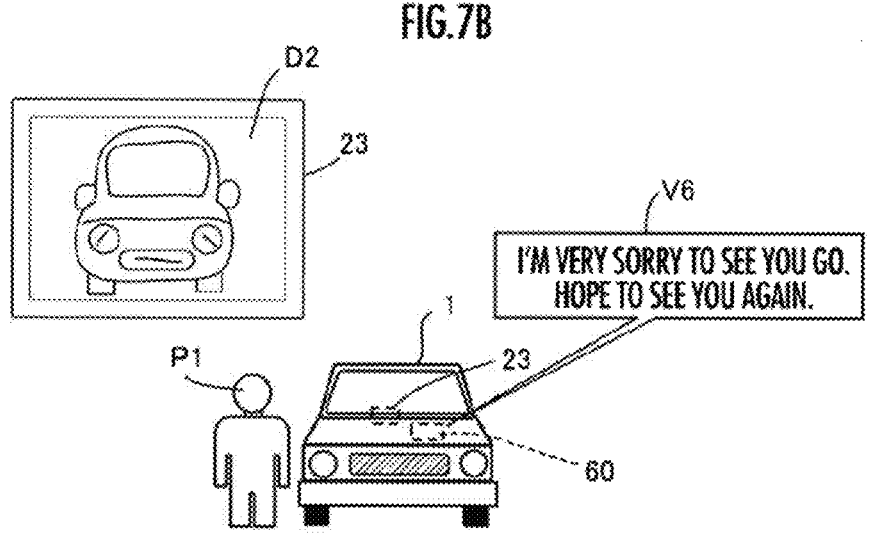

In STEP 7, the vehicle emotion notification unit 71 notifies that the vehicle 1 feels sad as illustrated in FIG. 7B. More specifically, the vehicle emotion notification unit 71 displays, on the display unit 23, an image D2 personifying the state in which the vehicle 1 feels sad, and at the same time outputs a voice V6 saying that "I'm very sorry to see you go. Hope to see you again." from the speaker 22 with a heavy tone.

Figure 8:
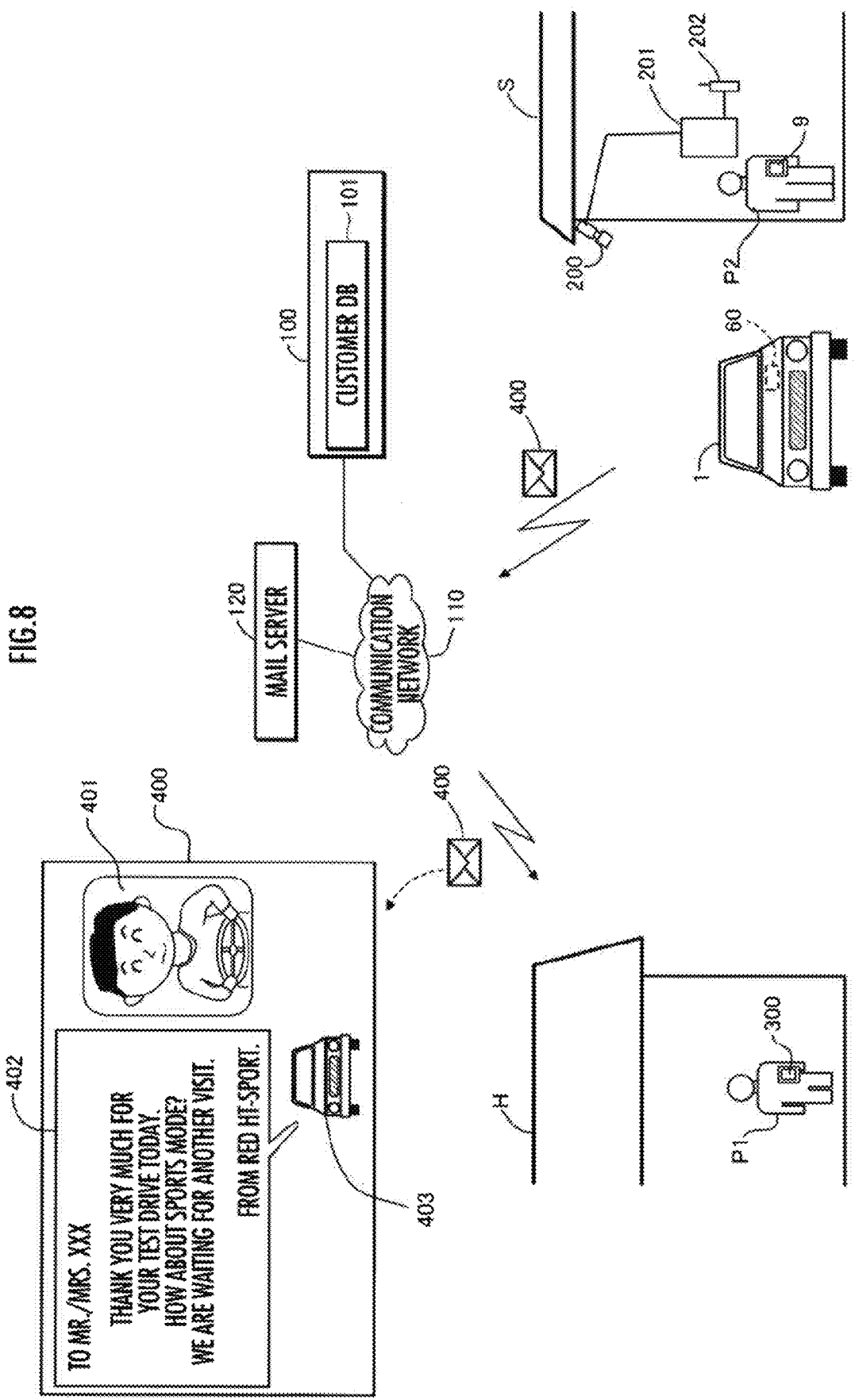
FIG. 8 is an explanatory view of a situation where a thank-you email is transmitted after the test drive is finished.

The following STEP 8 is a process performed by the image transmission unit 70. The image transmission unit 70 extracts the address of the test driver P1 from the customer data of the test driver P1. With reference to FIG. 8, the image transmission unit 70 calculates the distance from the store S (test drive ending location) to a home H of the test driver P1 to predict the time (expected time to return home) for the test driver P1 to return to the home H.

Then, when the time reaches the expected time to return home, the image transmission unit 70 transmits an email 400 expressing appreciation for the test drive to a communication terminal 300 (a smartphone, a tablet, a mobile phone, and the like) of the test driver P1 via a mail server 120.

The email 400 contains an image 401 of the test driver P1 captured in STEP 10 of FIG. 4 or in STEP 40 of FIG. 5; a thank-you document 402; and an image 403 of the vehicle 1 or a vehicle of the same type and the same color as the vehicle 1.

Since the image 401 of the test driver P1 is an image captured when the emotion level of "like" of the test driver P1 is increased by a predetermined level or more, the image 401 is basically a smile image. If a plurality of images are captured, smile detection is performed on each image, and an image with the highest smile level may be selected from among the detected smile images and may be used as the image 401 of the test driver P1 to be attached to the email 400.

Further, the addresser of the email 400 is a vehicle type name (illustrated by "HT-SPORT" in FIG. 8) of the vehicle 1, which can enhance the impression of the test driver P1 to this type of vehicle by including the image 403 of the vehicle 1 or a vehicle of the same type and the same color as the vehicle 1.

4. Other Embodiments

The above embodiment has been described using an example where the test driver P1 performs test drive of the vehicle 1. When the user uses his or her own vehicle, the user can be made to recognize the usefulness of the current vehicle by providing information on the specific function assumed to interest the user in the same manner as described above.

In the above embodiment, a still image (image 401) of the test driver P1 is attached to the email 400, but a moving image of the user P1 may be attached thereto. Further, when the image of the test driver P1 is captured, data of the voice emitted by the test driver P1 may be recorded and attached to the email together with the image. Furthermore, when the test rider P1 has contracted the purchase of the vehicle, the contract date, the expected delivery date, and the like may be included in the email and the image information.

In the above embodiment, in STEP 8 of FIG. 4, the image transmission unit 70 sends an email to the test driver P1 by assuming the time for the test driver P1 to return home, but the email may be sent to the test driver P1 when it is estimated or detected that the user P1 has left the predetermined area including the vehicle 1. In this case, the image transmission unit 70 may recognize that the user P1 has left the predetermined area including the vehicle 1, for example, (1) when a predetermined time has elapsed from when it was recognized from the images and the like captured by the cameras 11, 13, and 20 that the user P1 left the vehicle 1, or (2) when a predetermined time has elapsed from when the user P1 ended the test drive of the vehicle 1 or the user performed the operation such as folding the seat.

The above embodiment comprises the action detection unit 65 and the emotion engine 66 and the function-of-interest estimation unit 67 estimates the specific function that interests the user based on the action of the user detected by the action detection unit 65 and the emotion of the user estimated by the emotion engine 66 when the action is detected. Alternatively, another embodiment may comprise only the action detection unit 65 and the function-of-interest estimation unit 67 may estimate the specific function based on the action of the user detected by the action detection unit 65. Alternatively, another embodiment may comprise only the emotion engine 66 and the function-of-interest estimation unit 67 may estimate the specific function that interests the user based on the emotion of the user P1 detected by the emotion engine 66.

The above embodiment has described the four-wheeled vehicle 1 as the moving body of the present invention, but the present invention may be applied to various types of moving bodies including other types of vehicles such as two-wheeled vehicles, ships, airplanes, and the like.

REFERENCE SIGNS LIST

1 vehicle (moving body)
50 control unit
51 communication device
60 information provision device
61 test drive recognition unit
62 current vehicle information acquisition unit
63 vehicle information acquisition unit
64 operation situation detection unit
65 action detection unit
66 emotion engine (emotion estimation unit)
67 function-of-interest estimation unit
68 surrounding situation recognition unit
69 information provision unit
70 image transmission unit
71 vehicle emotion notification unit
100 customer information server
101 customer database
400 email
P1 test driver
P2 salesperson

The invention claimed is:

1. An information provision device which functions in a moving body, the information provision device comprising:
  a function-of-interest estimation unit which estimates a specific function that interests a user from among functions possessed by the moving body based on either one or both of the estimated emotion of the user who uses the moving body and an action performed on the moving body by the user;
  an information provision unit which provides the user with information on the specific function;
  a test drive recognition unit which recognizes that the user is test-driving the moving body; and
  a current moving body information acquisition unit which acquires information on a current moving body owned by the user, wherein
  while the test drive recognition unit recognizes that the user is test-driving the moving body, the information provision unit provides the user with information on the specific function of the current moving body recognized from the information on the current moving body together with the information on the specific function of the moving body that the user is test-driving.

2. The information provision device according to claim 1, further comprising
  an operation situation detection unit which detects an operation performed by the user on an operation unit provided in the moving body, wherein
  an action performed on the moving body by the user is detected based on a detection result of the operation situation detection unit.

3. The information provision device according to claim 1, wherein
  the information provision unit provides information encouraging operation for using the specific function as the information on the specific function.

4. The information provision device according to claim 1, further comprising
  a surrounding situation recognition unit which recognizes a situation around the moving body, wherein
  when the specific function is a function for improving driving performance, on condition that the surrounding situation recognition unit recognizes that the road on which the moving body is moving is empty, the information provision unit provides information encouraging operation for using the specific function.

5. The information provision device according to claim 1, wherein
  while the test drive recognition unit recognizes that the user is test-driving the moving body, the information provision unit provides the user with information on the specific function of a competing moving body competing with the moving body that the user is test-driving, together with the information on the specific function of the current moving body and the moving body that the user is test-driving, the competing moving body being from a brand of the current moving body recognized from the information of the current moving body.

6. The information provision device according to claim 1, further comprising:
  a notification unit which notifies the user; and
  a moving body emotion notification unit wherein while the test drive recognition unit recognizes that the user is test-driving the moving body, the notification unit notifies that the moving body is happy, and when it is switched from a state in which the test drive recognition unit recognizes that the user is test-driving the moving body, to a state in which the test drive recognition unit does not recognize that the user is test-driving the moving body, the notification unit notifies that the moving body feels sad.

7. A moving body comprising the information provision device according to claim 1.

8. An information provision device which functions in a moving body, the information provision device comprising:
  a function-of-interest estimation unit which estimates a specific function that interests a user from among the functions possessed by the moving body based on either one or both of the estimated emotion of the user who uses the moving body and an action performed on the moving body by the user;
  an information provision unit which provides the user with information on the specific function;
  a test drive recognition unit which recognizes that the user is test-driving the moving body; and
  a current moving body information acquisition unit which acquires information on a current moving body owned by the user, wherein
  while the test drive recognition unit recognizes that the user is test-driving the moving body, the information provision unit provides the user with information on the specific function of a competing moving body competing with the moving body that the user is test-driving from a brand of the current moving body recognized from the information of the current moving body, together with the information on the specific function of the moving body that the user is test-driving.

9. The information provision device according to claim 8, further comprising an operation situation detection unit which detects an operation performed by the user on an operation unit provided in the moving body, wherein an action performed on the moving body by the user is detected based on a detection result of the operation situation detection unit.

10. The information provision device according to claim 8, wherein the information provision unit provides information encouraging operation for using the specific function as the information on the specific function.

11. The information provision device according to claim 8, further comprising a surrounding situation recognition unit which recognizes a situation around the moving body, wherein when the specific function is a function for improving driving performance, on condition that the surrounding situation recognition unit recognizes that the road on which the moving body is moving is empty, the information provision unit provides information encouraging operation for using the specific function.

12. The information provision device according to claim 8, wherein while the test drive recognition unit recognizes that the user is test-driving the moving body, the information provision unit provides the user with information on the specific function of a competing moving body competing with the moving body that the user is test-driving, together with the information on the specific function of the current moving body and the moving body that the user is test-driving, the competing moving body being from a brand of the current moving body recognized from the information of the current moving body.

13. The information provision device according to claim 8, further comprising:

a notification unit which notifies the user; and a moving body emotion notification unit wherein while the test drive recognition unit recognizes that the user is test-driving the moving body, the notification unit notifies that the moving body is happy, and when it is switched from a state in which the test drive recognition unit recognizes that the user is test-driving the moving body, to a state in which the test drive recognition unit does not recognize that the user is test-driving the moving body, the notification unit notifies that the moving body feels sad.

14. A moving body comprising the information provision device according to claim 8.

* * * * *